(12) United States Patent
Barati et al.

(10) Patent No.: US 11,185,467 B2
(45) Date of Patent: Nov. 30, 2021

(54) VIBRATORY UNLOADING KNEE BRACE FOR KNEE OSTEOARTHRITIS

(71) Applicants: Kourosh Barati, Tehran (IR); Mokhtar Arazpour, Tehran (IR); Ismail Ebrahimi Takamjani, Tehran (IR)

(72) Inventors: Kourosh Barati, Tehran (IR); Mokhtar Arazpour, Tehran (IR); Ismail Ebrahimi Takamjani, Tehran (IR)

( * ) Notice: Subject to any disclaimer, the term of this patent is extended or adjusted under 35 U.S.C. 154(b) by 989 days.

(21) Appl. No.: 15/874,846

(22) Filed: Jan. 18, 2018

(65) Prior Publication Data

US 2018/0140505 A1 May 24, 2018

(51) Int. Cl.
*A61H 23/02* (2006.01)
*A61F 5/01* (2006.01)

(52) U.S. Cl.
CPC ........... *A61H 23/02* (2013.01); *A61F 5/0123* (2013.01); *A61H 23/0254* (2013.01); *A61F 2005/0134* (2013.01); *A61F 2005/0139* (2013.01); *A61F 2005/0144* (2013.01); *A61F 2005/0146* (2013.01); *A61F 2005/0155* (2013.01); *A61F 2005/0172* (2013.01); *A61H 2201/0192* (2013.01); *A61H 2201/149* (2013.01); *A61H 2201/165* (2013.01); *A61H 2201/1642* (2013.01); *A61H 2201/1664* (2013.01); *A61H 2201/5002* (2013.01); *A61H 2201/5058* (2013.01); *A61H 2205/102* (2013.01)

(58) Field of Classification Search
CPC ................. A61H 23/02; A61H 23/0254; A61H 23/0218; A61H 23/0236; A61H 23/0245; A61H 23/0263; A61H 1/00; A61H 1/024; A61H 39/007; A61H 2023/0209; A61H 2023/0227; A61H 2023/0281; A61H 2023/029; A61H 3/00–068; A61H 2003/001–065; A61F 5/0123; A61F 2005/0134; A61F 2005/0139; A61F 2005/0144; A61F 2005/0146; A61F 2005/0155; A61F 2005/0172
USPC .......................................................... 601/46
See application file for complete search history.

(56) References Cited

U.S. PATENT DOCUMENTS

| 3,030,950 A * | 4/1962 | Forthun ............. A61H 23/0263 |
| | | 601/46 |
| 3,601,122 A * | 8/1971 | Guertin .................. A61G 13/00 |
| | | 601/111 |
| 6,746,414 B1 | 6/2004 | Devreese |
| 7,507,215 B2 | 3/2009 | Ryan |
| 7,610,100 B2 | 10/2009 | Jaax et al. |
| 8,425,579 B1 | 4/2013 | Edelman et al. |
| 9,439,797 B2 | 9/2016 | Baym et al. |
| 2009/0221943 A1* | 9/2009 | Burbank ............ A61N 1/36021 |
| | | 601/46 |

(Continued)

*Primary Examiner* — Valerie L Woodward
*Assistant Examiner* — Paige Kathleen Bugg
(74) *Attorney, Agent, or Firm* — NovoTechIP International PLLC

(57) ABSTRACT

A knee device and method of stimulating muscles is disclosed. The knee device includes a knee brace with a support frame and vibration components. The vibration components are connected to the support frame by adjustable arms that allow for precise adjustments in the spatial position and orientation of the vibration components. The vibration components can be activated by the ambulation of a user.

19 Claims, 12 Drawing Sheets

(56) References Cited

U.S. PATENT DOCUMENTS

2012/0196729 A1* 8/2012 Rafaeli ............ A63B 21/00196
                                                      482/110
2017/0266077 A1* 9/2017 Mackin ................ A61G 13/125

* cited by examiner

VIBRATORY UNLOADING KNEE BRACE FOR KNEE OSTEOARTHRITIS

BACKGROUND

Osteoarthritis (OA) results from hyaline cartilage degeneration. OA is the most prevalent systematic disease in the synovial joints like those associated with the knee. OA causes pain and muscular activity, as well as issues with proprioception and deficits in knee stability. Knee OA, also referred to as KOA, interferes with activities of daily living (ADL) by limiting physical function and, in particular, ambulation. Knee OA prevalence has been reported as ranging between 8.1-16%. The annual cost of knee OA pain management is about 51 billion in the United States of America alone. The burdens on health care resources and on the economy caused by KOA are substantial. Various forms of conservative treatments, including medication, physical therapy, and orthotics have been investigated as potential methods of KOA management.

In some cases, sufferers of KOA are prescribed the use of unloader knee braces. For example, individuals with medial compartment knee osteoarthritis (OA) may utilize such braces to help unload the damaged compartment. However, these orthoses, despite providing some advantages, can lead to a reduction in the surrounding knee muscular activity. This reduction leads to muscle atrophy that results in knee OA progression. In order to address this, local muscle vibration has been used to help increase muscle activity, thereby increasing muscular activity and reducing pressure associated with the damaged knee compartment. It is important to note that muscle activation timing is an important issue in walking and each muscle group has peak activation during different phases of the gait cycle. Therefore, it is anticipated that orthoses configured to activate the suitable part of muscle groups during the appropriate phase of a gait cycle would be useful in rehabilitation of subjects with knee OA. There is a need in the art for a vibration orthotics that can be easily applied by a user, worn comfortably throughout the day, and provide such restorative benefits to the physiological regions associated with KOA.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

In one general aspect, the present disclosure is directed to a device for the stimulation of muscles. The device includes a support frame, where the support frame includes an intermediate portion extending between an upper bar and a lower bar. The intermediate portion further includes a primary hinge, where the primary hinge is configured to facilitate a bending of the upper bar relative to the lower bar. The device also includes a first arm assembly, the first arm assembly including a first elongated segment and a second elongated segment. A first end portion of the first elongated segment is adjustably secured to the upper bar, and a second end portion of the first elongated segment is adjustably secured to a third end portion of the second elongated segment. Furthermore, the device includes a first vibration component mounted on a fourth end portion of the second elongated segment, where the first vibration component is configured to generate vibrations.

The above general aspect may include one or more of the following features. In one example, the device also includes a second arm assembly and a second vibration component, where the second arm assembly is adjustably secured to the lower bar, and the second vibration component is mounted on the second arm assembly. In some cases, there is a third arm assembly and a third vibration component, where the third arm assembly is adjustably secured to the upper bar, and the third vibration component is mounted on the third arm assembly. In another example, the device can include a first switch device, where the first switch device is activated in response to a compressive force. In some implementations, the first vibration component is configured to generate vibrations in response to an activation signal generated by the first switch device. In another implementation, the device includes both a first switch device and a second switch device, where the first vibration component is configured to generate vibrations in response to an activation signal generated by the first switch device, and where the second vibration component is configured to generate vibrations in response to an activation signal generated by the second switch device. In some cases, the third vibration component is configured to generate vibrations in response to the activation signal generated from the first switch device. As another example, the first segment may be capable of both translational motion and rotational motion, and/or the second segment can be capable of both translational motion and rotational motion. In one implementation, the first vibration component is capable of rotational motion. In another implementation, the first vibration component has five degrees of freedom. Furthermore, the device may also include a first shell, where the first shell is attached to the upper bar, and the first shell includes a first cuff portion sized and dimensioned to wrap around a thigh region of a person. In some cases, the device also has a second shell, where the second shell is attached to the lower bar, and the second shell includes a second cuff portion sized and dimensioned to wrap around a calf region of a person. In another example, the device further includes a control unit, the control unit being configured to receive the activation signal and activate a motor in the first vibration component.

In another general aspect, the present disclosure is directed to a method of providing stimulation to muscles. The method can include securing a knee brace to a leg of a user, the knee brace including a first arm assembly connected to a support frame, and a vibration component being mounted on an end of the first arm assembly. The method also includes adjusting the first arm assembly by sliding a first elongated segment of the first arm assembly along a first direction that is substantially perpendicular to a first longitudinal axis of the leg, where the first elongated segment is elongated in the first direction. In addition, the method may include rotating the first vibration component until an end of a stimulator shaft protruding from a housing of the first vibration component directly faces toward a region of the leg where muscle stimulation is desired, as well as compressing a first switch device, thereby activating the first vibration component. The method can also include delivering vibrational stimulation to the first region of the leg via the stimulator shaft.

The above general aspect may include one or more of the following features. In one example, adjusting the first arm assembly can further include sliding a second elongated segment of the first arm assembly along a second direction that is substantially perpendicular to the first direction, where the second elongated segment is elongated in the second direction. In another example, adjusting the first arm assembly further includes rotating the first elongated segment about a second longitudinal axis of the first elongated segment. In addition, in some implementations, adjusting the first arm assembly further includes rotating the second elongated segment about a third longitudinal axis of the second elongated segment, the third longitudinal axis being substantially perpendicular to the first longitudinal axis. In some cases, compressing the first switch device further includes the user taking at least a first step with the leg on which the knee device is secured. In another implementation, the method includes ceasing delivery of the vibrational stimulus when the compressive force on the first switch device is released.

Other systems, methods, features and advantages of the implementations will be, or will become, apparent to one of ordinary skill in the art upon examination of the following figures and detailed description. It is intended that all such additional systems, methods, features and advantages be included within this description and this summary, be within the scope of the implementations, and be protected by the following claims.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1:
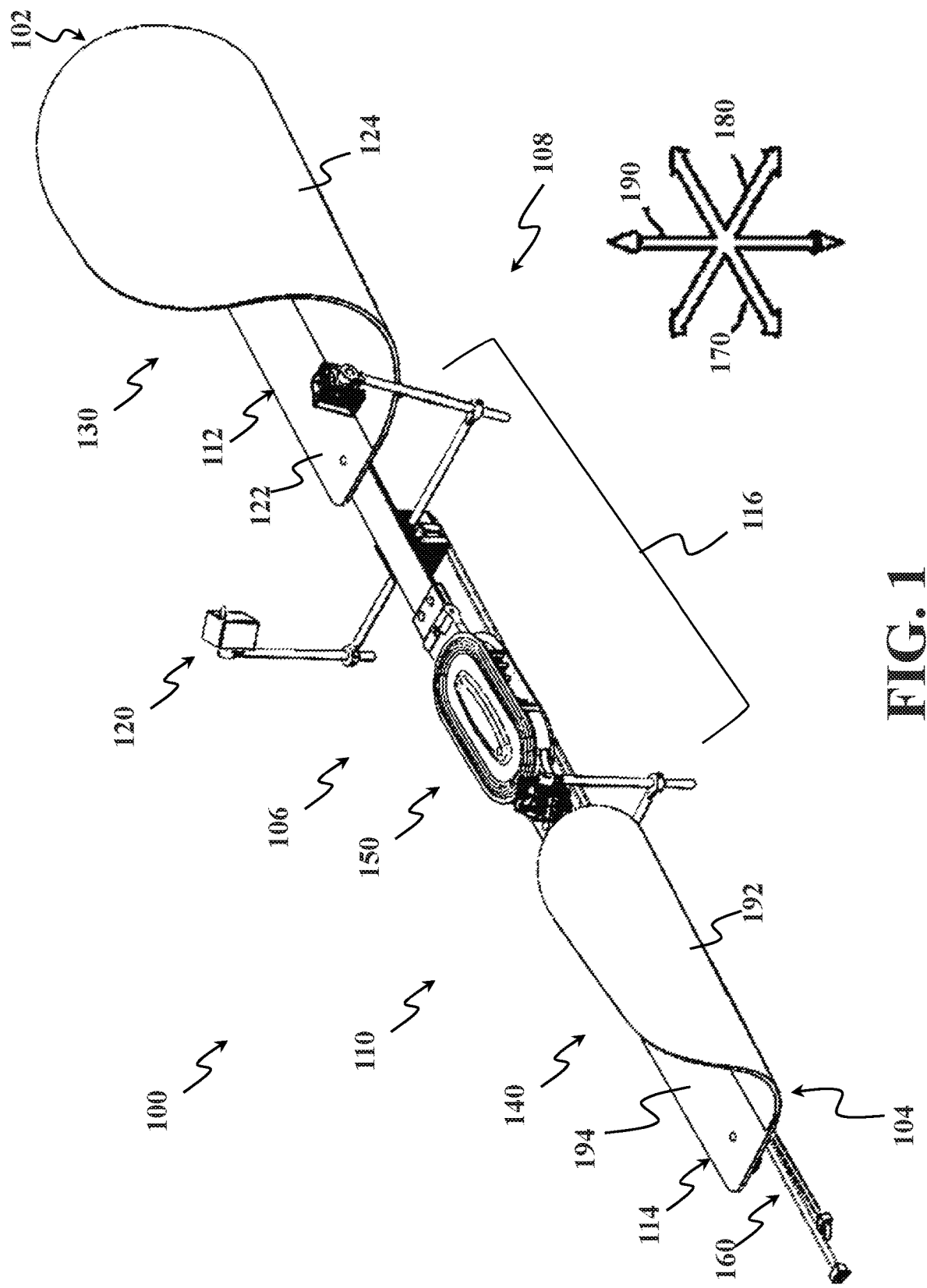
FIG. 1 is an isometric illustration of an implementation of a knee brace device.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary implementations of the present disclosure. For purposes of explanation, specific nomenclature is set forth to provide a thorough understanding of the present disclosure. However, it will be apparent to one skilled in the art that these specific details are not required to practice the disclosed exemplary implementations. Descriptions of specific exemplary implementations are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

As will be discussed herein, systems and methods directed to a knee joint brace device ("knee device") for treatment of osteoarthritis are disclosed. The systems and methods may include the usage of a knee brace or cage as well as vibration components for individuals who have been diagnosed with osteoarthritis of the knee or who otherwise suffer from knee joint-related conditions.

Osteoarthritis is among the most common systematic conditions associated with the joints of the knee. This condition is known to be a destructive joint disease that causes pain and contributes to functional problems such as losses in muscle strength, depth sense, and muscular stability. Knee osteoarthritis (KOA) has a major effect on daily physical functions and can lead to mild to severe functional limitations. KOA is caused by the destruction of joint cartilage, changes to the bones beneath the cartilage, osteophyte growth at bone edges, and weakness of muscles around the joint.

Generally, it is understood that there are two kinds of sensory fibers that are different in respect to the kind of potentials they generate: Type I (including Ia and Ib), and Type II. The Type Ia fibers are the largest and fastest fibers, and they fire when the muscle is stretching. Type Ia fibers essentially supply proprioceptive or balance information about the rate of change of its respective muscle. The muscles and sensory fibers surrounding the knee play an important role as active stabilizers and are crucial in protection of the joint structures against damaging influences. This is true in particular with respect to the Type Ia muscle fibers. In people suffering from knee osteoarthritis, a weakness in the quadriceps femoris muscle is evident. The muscle in individuals with knee osteoarthritis is about 20-40 percent weaker relative to healthy people of the same age and gender. The weakness in the quadriceps femoris muscle generally leads to an increase in joint loading of the knee, which frequently results in further damage to joint cartilage.

In many cases, the symptoms of the condition can arise from a failure in strengthening the muscles around the knee joint. Thus, stimulation of afferent Type Ia sensory fibers and/or other parts of the surrounding muscle provides a means of increasing the functionality of these muscles. As will be discussed herein, one approach that can provide such beneficial stimulation is the transmission of localized vibration, or physical oscillations, through the outer body to the muscles. For example, if vibration is transmitted to a muscle tendon while walking, the activity level of the associated muscle will increase. Thus, a device in which vibration can be provided to the muscles around the knee can help reduce the detrimental effects of osteoarthritis. The knee device disclosed here can be used to provide all-day reliable and localized stimulation of afferent type Ia sensory fibers in individuals suffering from knee osteoarthritis.

Figure 2:
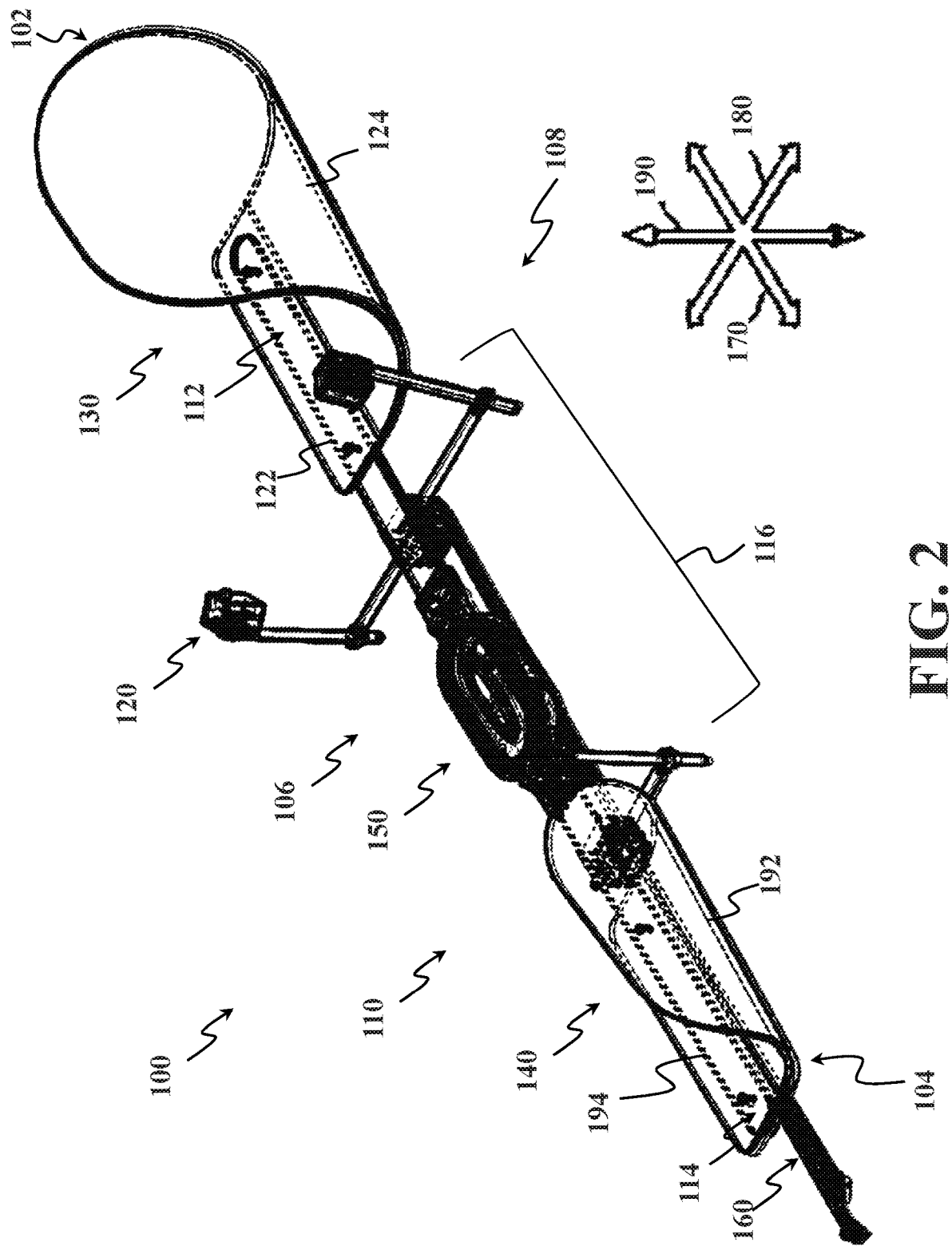
FIG. 2 is an isometric illustration of an implementation of a knee brace device.

Referring to FIGS. 1 and 2, one implementation of a knee device is illustrated. FIG. 1 presents an isometric view of an implementation of the knee device ("device") 100, and FIG. 2 presents a similar view with dotted lines to indicate portions of the device 100 that are not visible in FIG. 1. A set of axes are also provided for purposes of reference, identified as a longitudinal axis 170, a lateral axis 180, and a vertical axis 190. As will be discussed below, the device 100 can comprise various multiple distinct portions or components that are joined together or otherwise associated with one another.

In the implementation of FIGS. 1 and 2, device 100 can be seen to include a support frame 110, a plurality of vibration components 120, a first shell 130, a second shell 140, a plurality of joint mechanisms ("joints") 150, and a switch portion 160. For purposes of reference, the support frame 110 can be understood to include three general portions: an upper strap or upper bar 112, a lower strap or lower bar 114, and an intermediate joint portion ("intermediate portion") 116. In one implementation, the intermediate portion 116 can be disposed or extend between the upper bar 112 and the lower bar 114. Furthermore, in some implementations, the upper bar 112, the intermediate portion 116, and the lower bar 114 can be connected or joined such that they form a substantially continuous and elongated portion that provide a resilient support structure to the device 100 and permit the stable attachment of additional components, as will be described below.

For consistency and convenience, directional adjectives are employed throughout this detailed description corresponding to the illustrated implementations. The term "longitudinal" as used throughout this detailed description and in the claims refers to a direction extending a length of device 100. In some cases, for example, a longitudinal direction may be understood to extend in a manner substantially parallel to longitudinal axis 170, or between a first edge 102 (running along the top portion of the first shell 130) and a second edge 104 (running along the bottom portion of the second shell 140). Also, the term "lateral" as used throughout this detailed description and in the claims refers to a direction extending a width of device 100. In one case, a lateral direction may be understood to extend in a manner substantially parallel to lateral axis 180, or between a first side 106 and a second side 108 of device 100. Furthermore, the term "vertical" as used throughout this detailed description and in the claims refers to a direction generally perpendicular to both the lateral direction and the longitudinal direction, or the direction substantially parallel to the vertical axis 190. In addition, the vertical direction extends in a direction extending between an outer side 192 and an inner side 194. For purposes of reference, outer side 192 refers generally to the side or surface that faces outward or away from the leg, and inner side 194 refers generally to the side or surface that faces inward or toward the leg when the device 100 is worn. Thus, inner side 194 includes surfaces or portions which can contact or be pressed against portions of the leg on which device 100 is worn.

In different implementations, the device 100 includes provisions for comfortable and stable use of the device. For example, first shell 130 can be applied to or worn around a thigh region or upper part of a human leg (above the knee). In addition, second shell 140 can be applied to or worn around a calf region or lower part of a human leg (below the knee). In some implementations, the curvature associated with the of the first shell 130 may correspond generally to the average curvature of an adult thigh, and the curvature of the second shell 140 may correspond generally to the average curvature of an adult calf, such as a "universal sizing design" that allows adjustments in the size of the device. However, in other implementations, each device can be customized and built according to the size and proportions of a specific individual, thereby maximizing comfort and wearability. In some other implementations, there may be standard sizes corresponding to gender and common anatomical proportions, such as thigh and calf circumferences and lengths. For example, the device can be made available in an extra-small (XS), small (S), medium (M), large (L), extra-large (XL), double-extra-large (2XL), and so forth. The sizes can be varied based on whether the device is intended for a female or male, or children.

In different implementations, each shell can include an anchor portion 122 and a cuff portion 124. Anchor portion 122 can be understood to include the portion that is substantially flat, or lies in a generally horizontal plane. Anchor portion 122 may be mechanically secured, joined, connected, or adhesively attached to a portion of the upper bar 112 of the support frame 110.

In addition, it can be seen that for each shell, cuff portion 124 extends outward and upward with a substantially concave inner surface. In some implementations, cuff portion 124 can vary in dimensions and shape as discussed above with respect to sizing. Furthermore, the inner surface and opposite facing outward surface of each shell can be substantially smooth, as shown in FIGS. 1 and 2. In other implementations, either or both of the inner surface and outer surface of the shell can include undulations, bumps, curvature, or other texturing patterns that can promote comfort, grip, and fit of the shell along the leg. Furthermore, in some implementations, there may be cushioning or a hygienic replaceable insert that can be disposed between the leg and the inner surface of the shell when the device is worn. It should be understood that in different implementations the device 100 can be secured to a leg using straps, buckles, clasps, hook and loop material, magnets, compression spring loading, or other such components.

The material of the shells can include one or more of polyethylene, cross-linked polyethylene, polyurethane and reticulated polyurethane, thermoplastic polyurethane (TPU), woven and nonwoven fabric composites, elastic materials such as spandex, materials providing excellent compression and can absorb muscles shocks in physical activity, microfibers, cotton, elastane, and materials that are skin-friendly, breathable and provide softness, as well as other materials known to provide water, humidity, fungus, and abrasion resistance.

As noted above, different components of the device 100 can be secured to portions of the support frame 110. In FIGS. 1 and 2, it can be seen that the first shell 130 is disposed above and attached to upper bar 112 and the second shell 140 is attached to lower bar 114. Each bar is generally an elongated member; for example, upper bar 112 extends between first edge 102 and the intermediate portion 116. Furthermore, lower bar 114 extends between intermediate portions 116 and second edge 104. The overall length of the device 100 can be understood to extend between first edge 102 and the end of the switch portion 160, where the switch portion 160 may be adjustable in length (see FIGS. 9 and 10).

Figure 3:
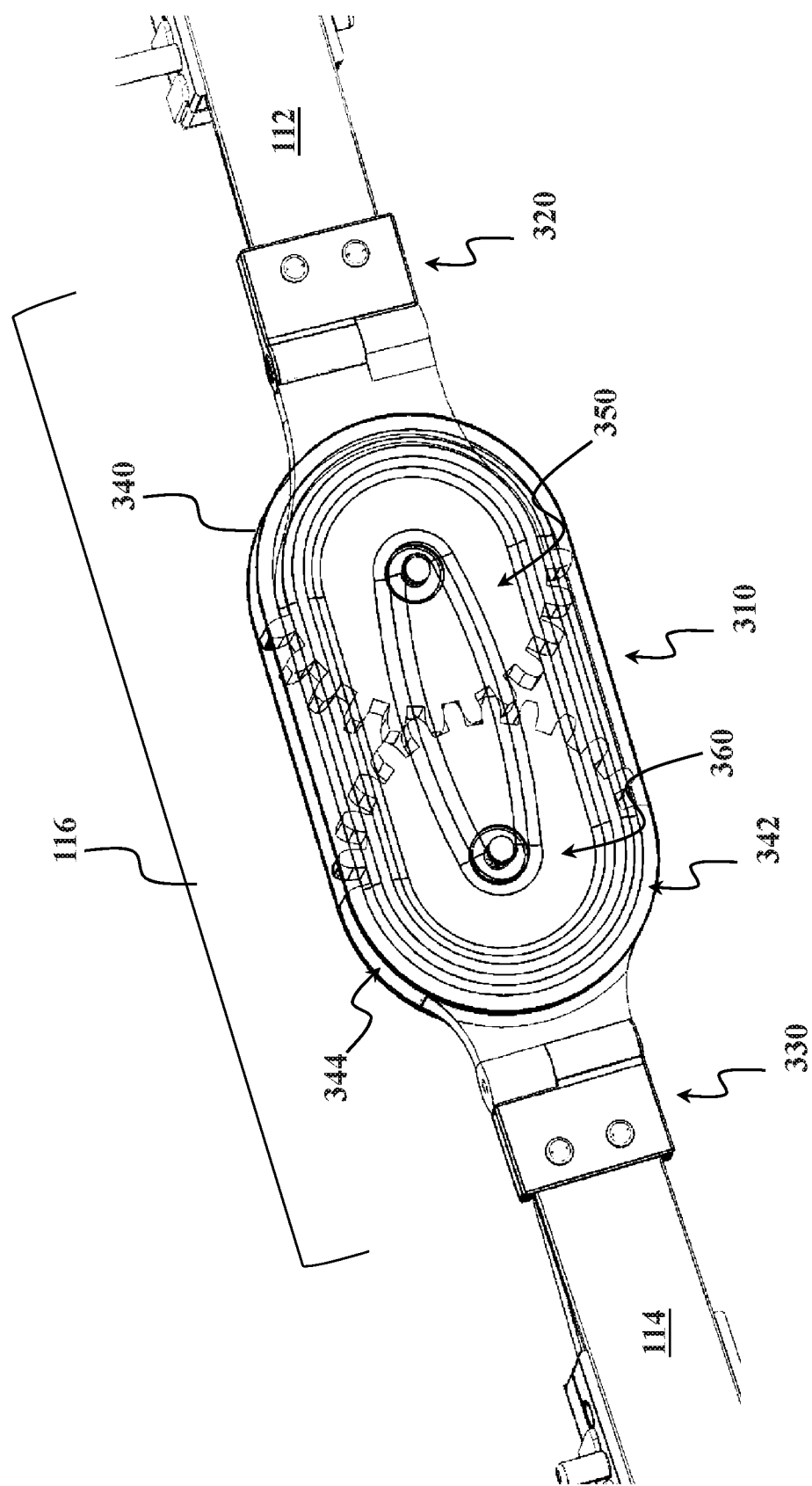
FIG. 3 is an isometric illustration of an implementation of joints of a knee brace device.
Figure 4:
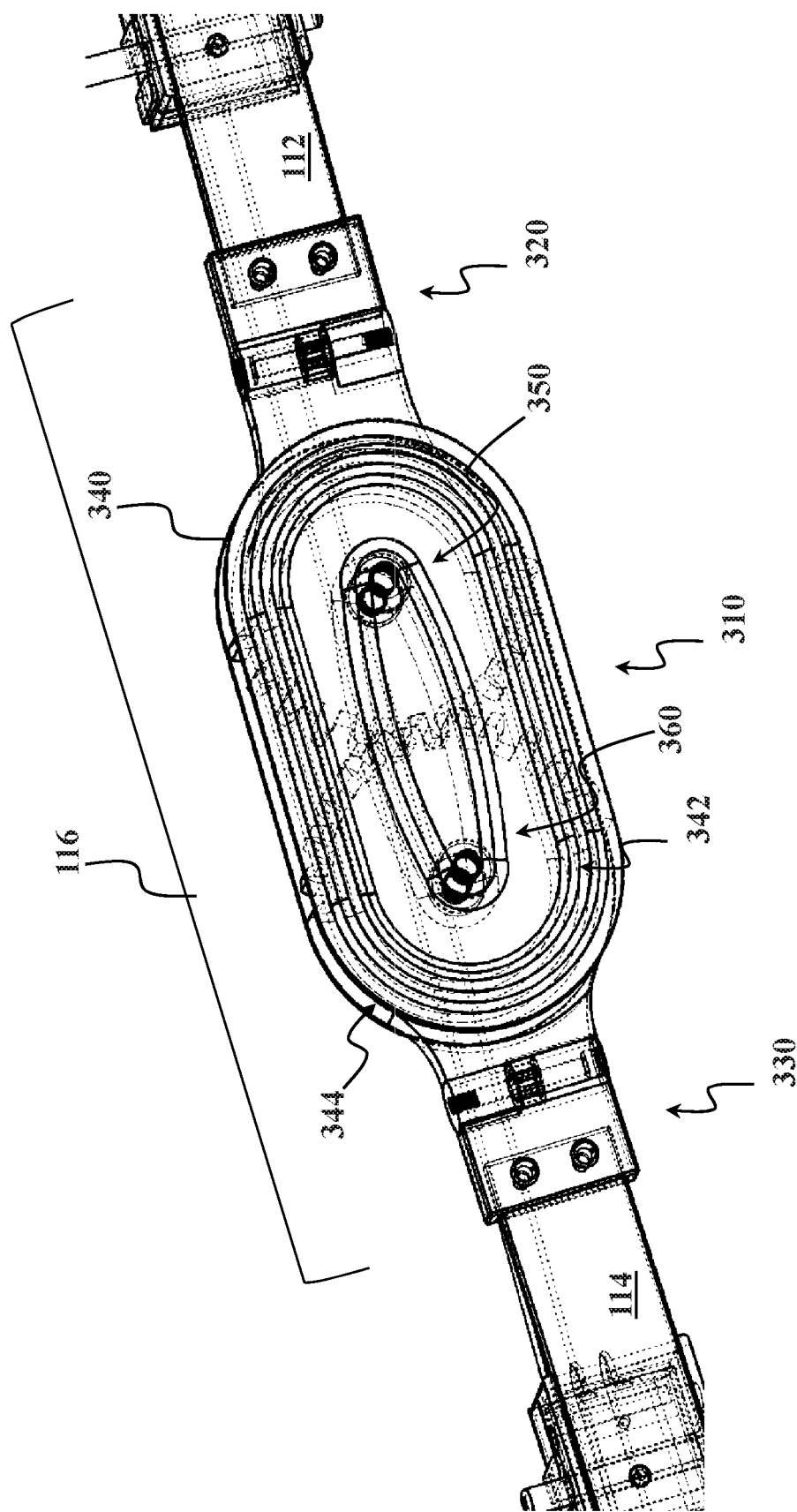
FIG. 4 is an isometric illustration of an implementation of joints of a knee brace device.

In different implementations, the device 100 includes provisions for accommodating the natural motion and movements of a leg. Referring now to FIGS. 3 and 4, an isolated magnified view of the intermediate portion 116 is depicted. FIG. 3 presents an isometric view of an implementation of the intermediate portion 116, and FIG. 4 presents a similar view with dotted lines to indicate interior components of the intermediate portion 116 that are not visible in FIG. 3. As shown in FIGS. 3 and 4, the intermediate portion 116 includes a primary gear hinge ("primary hinge") 310 disposed between a first hinge joint ("first hinge") 320 and a second hinge joint ("second hinge") 330. It can be understood that the primary hinge 310 is configured to facilitate an elastic bending of the knee brace for accommodating the natural range of motion of a leg during use. Thus, in one implementation, the primary hinge works to permit repeated bending of the knee brace such that the upper bar and the lower bar can move relative to one another. The support frame can be understood to extend in a generally linear or flat initial position and transition to a variety of bent or curved positions where an angle between the upper bar and lower bar can vary widely.

In some implementations, the primary hinge 310 can include a housing 340 with an inner cover 342 and an outer cover 344. As shown in FIG. 4, the housing 340 can support and/or protect the engagement and motion between a first gear 350 and a second gear 360. Each gear includes a plurality of teeth which are intermeshed with the teeth of the opposing gear, permitting pivotable motion. It will be appreciated that the housing 340 is shown as an example, and the housing can include different shapes and sizes depending on the application and user. In one implementation, the teeth of the first gear 350 and the teeth second gear 360 are intermeshed and engaged with one another in all positions of relative rotation between the arms. In some cases, this arrangement helps prevent injury of the knee by guiding the knee into positions where there is less potential for or a likelihood of traumatization of the knee, especially undesired hyperextension.

In addition, in different implementations, first hinge 320 and second hinge 330 can be configured to provide valgus and varus adjustment to fit individual's alignment. The first hinge 320 is disposed between the primary hinge 310 and the first shell 130 associated with the thigh region, and second hinge 330 is disposed between the primary hinge 310 and the second shell 140 associated with the calf region. Thus, the inclusion of each hinge at their respective positions allows the brace to be adjusted to accommodate an individual's gait or stance. For example, the first hinge 320 and second hinge 330 can provide protection in conditions known as a valgus deformity ("knock-kneed"), an outward rotation of the tibia on the femur. The hinges can also provide protection for individuals with a condition known as a varus deformity, an inward rotation of the tibia, resulting in a leg that appears bowed out ("bowlegged"). Both conditions can lead to misalignments of the hip or knee, potentially causing injury and knee pain. In some implementations, the hinges can help reduce the effects of these conditions.

Figure 5:
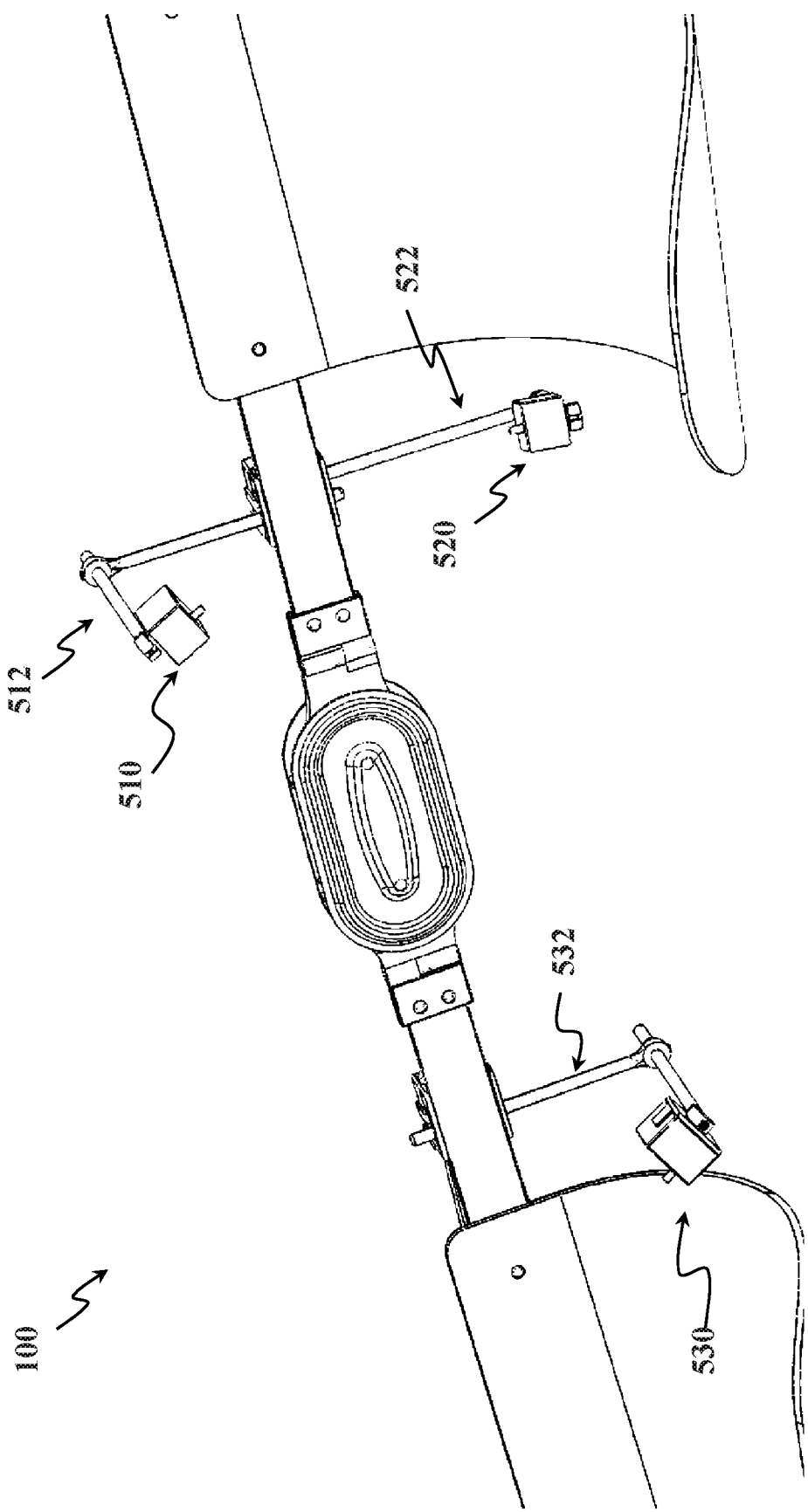
FIG. 5 is an isometric illustration of an implementation of vibration components of a knee brace device.
Figure 6:
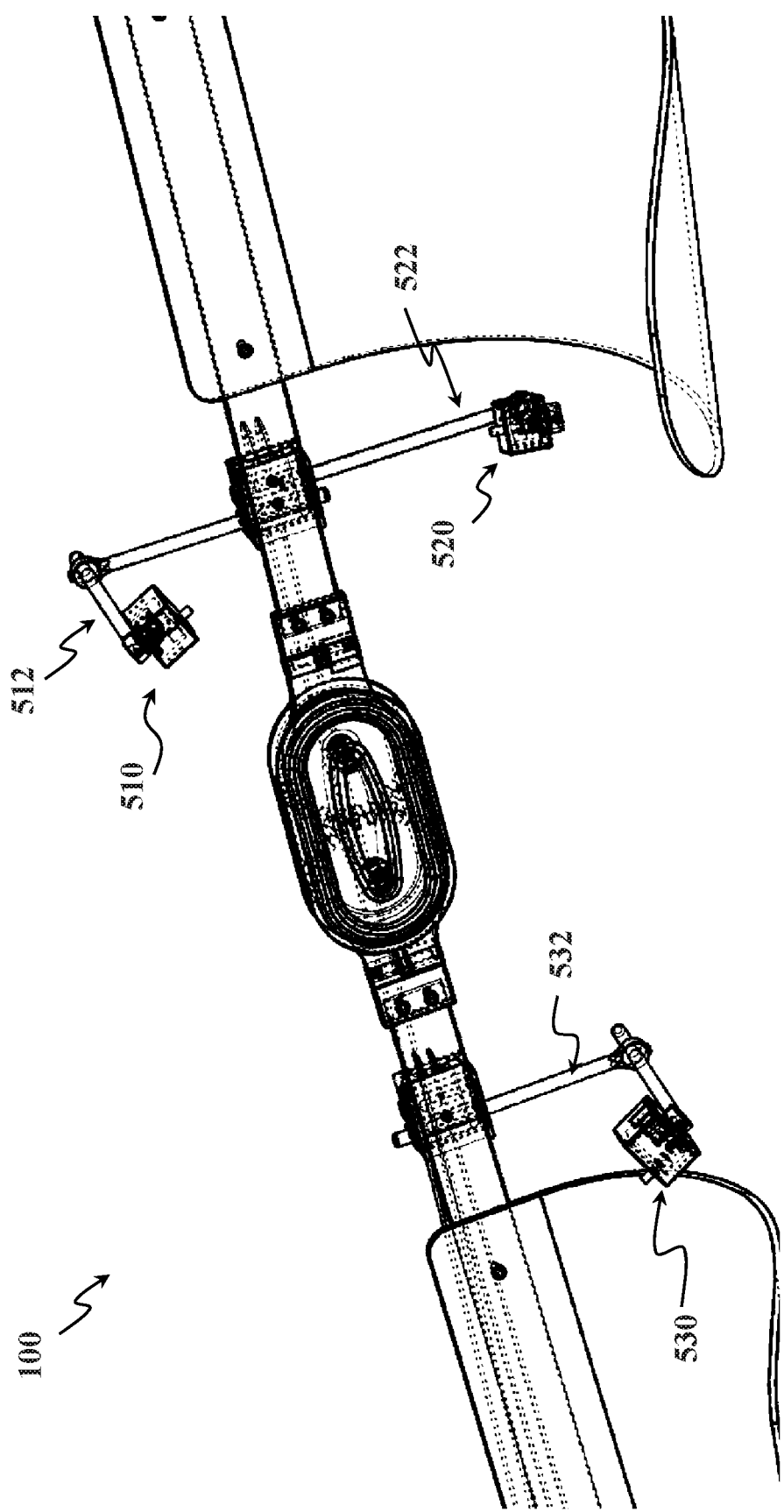
FIG. 6 is an isometric illustration of an implementation of vibration components of a knee brace device.

Referring now to FIGS. 5-8, additional details are provided with respect to the vibration features of the device 100. In FIGS. 5 and 6, an isolated magnified view of a central portion of the device 100 is depicted. FIG. 5 presents an isometric view of an implementation of the central portion, and FIG. 6 presents a similar view with dotted lines to indicate components of the central portion that are not visible in FIG. 5.

In different implementations, the device 100 includes a plurality of vibration components. As noted earlier, in one implementation, the device 100 includes three vibration components. However, in other implementations, there may be additional or fewer vibration components included in the device. In FIGS. 5 and 6, it can be seen that device 100 includes a first vibration component ("first component") 510, a second vibration component ("second component") 520, and a third vibration component ("third component") 530. Each vibration component is secured to an arm assembly. Furthermore, it can be seen that first component 510 is secured to a first arm assembly ("first arm") 512, second component 520 is secured to a second arm assembly ("second arm") 522, and third component 530 is secured to a third arm assembly ("third arm") 532. In other implementations, there may be additional vibration components secured to additional arms, or there may be more than one vibration component secured to a single arm. In addition, in some other implementations, there can be vibration components disposed on the support frame and/or attached to the shells.

In different implementations, the first component 510 is configured for stimulation of the Quadriceps Femoris Muscle region. Thus, this vibrator component is located above the knee joint and in the front when the device is worn. In addition, the second component 520 is configured for stimulation of the Hamstring Muscle region. This vibrator is associated with the region above the knee joint and in the back when the device is worn. Furthermore, the third component 530 is configured to stimulate the Gastrocnemius Muscle region. Therefore, this vibrator is located below the knee joint and in the back when the device is worn.

In different implementations, the device can include provisions for maneuvering and adjusting the position of each vibration component relative to the leg. As identified above, vibration components can be mounted on various types of moveable and adjustable arms in some implementations. For purposes of simplicity, only one arm (third arm 532) will be discussed herein. However, it should be understood that in some implementations the features and properties of third arm 532 are applicable to other arm assemblies. Thus, first arm 512 and/or second arm 522 can be understood to be substantially similar in function and design as third arm 532 in one implementation.

Figure 7:
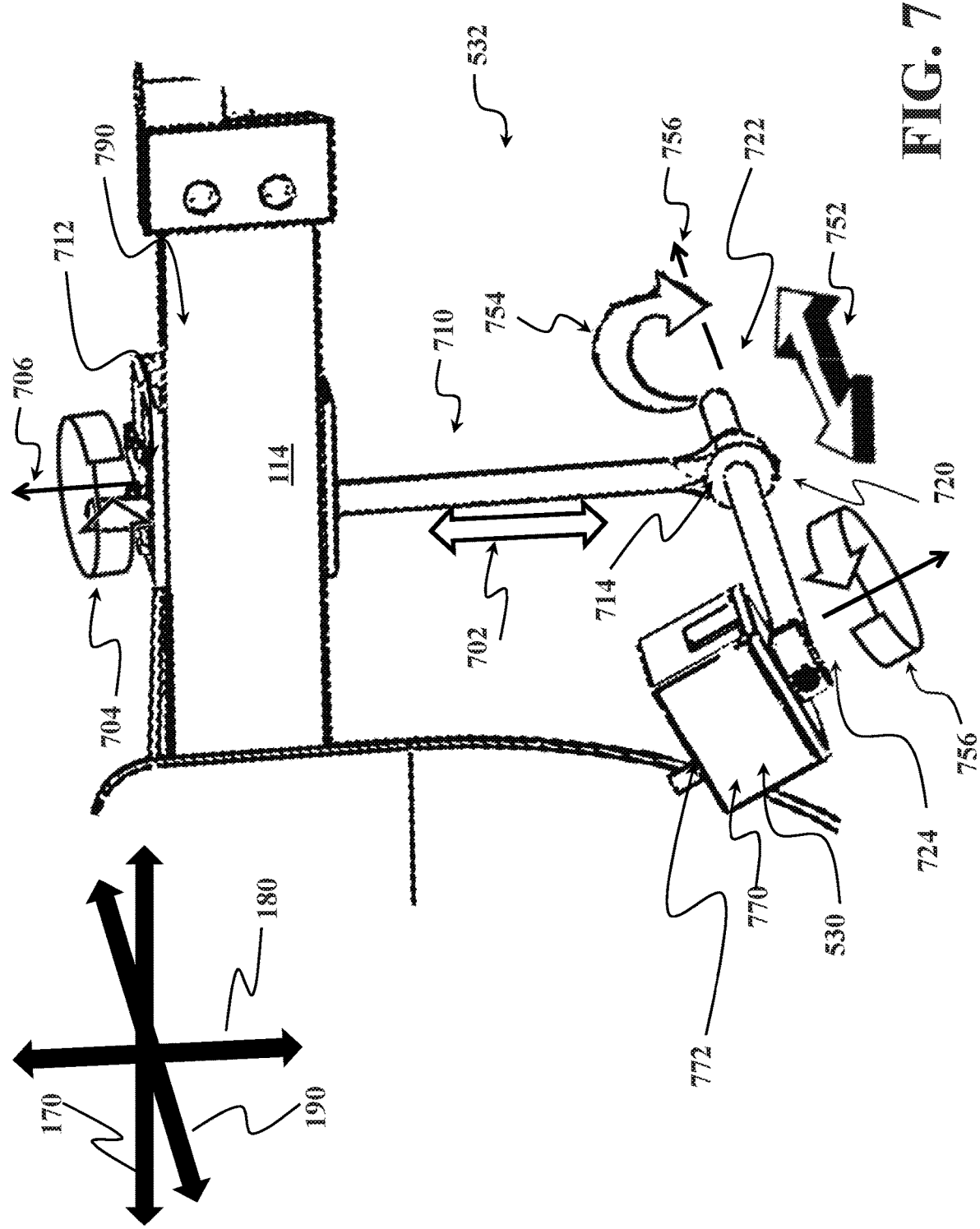
FIG. 7 is an illustration of an implementation of a vibration component of a knee brace device and its corresponding arm assembly.

As shown in FIG. 7, in one implementation, third arm 532 includes a first elongated bar segment ("first segment") 710 and a second elongated bar segment ("second segment") 720. The first segment 710 and/or second segment 720 can include an elongated bar or rod, or other substantially rigid elongated shape. In one implementation, each segment may include a substantially round cross-section, though some portions can include variations in size and shape (for example, see looped portion of the receiving end 714 identified below). In one implementation, a segment may include other cross-sectional shapes such as pentagonal, hexagonal, or other shapes. In addition, in some cases, some surface portions of a segment can include texturing that allows an easier grip by a user.

For purposes of reference, first segment 710 can be understood to extend between a first end portion or an anchoring end portion ("anchoring end") 712 and a second end portion or receiving end portion ("receiving end") 714, where the anchoring end 712 is movably connected or adjustably secured through a base portion 790 to the lower bar 114. For purposes of this description, the terms adjustably secured or movably connected refer to a stable, firm attachment or link between two components or parts, where at least one of the two parts can continue to move relative to the second part while the two parts are secured to one another. In addition, with respect to the adjustably secured components described herein, if a part is moved or adjusted, it is configured to remain generally stable in the new position and orientation until moved again by an external force.

Figure 10:
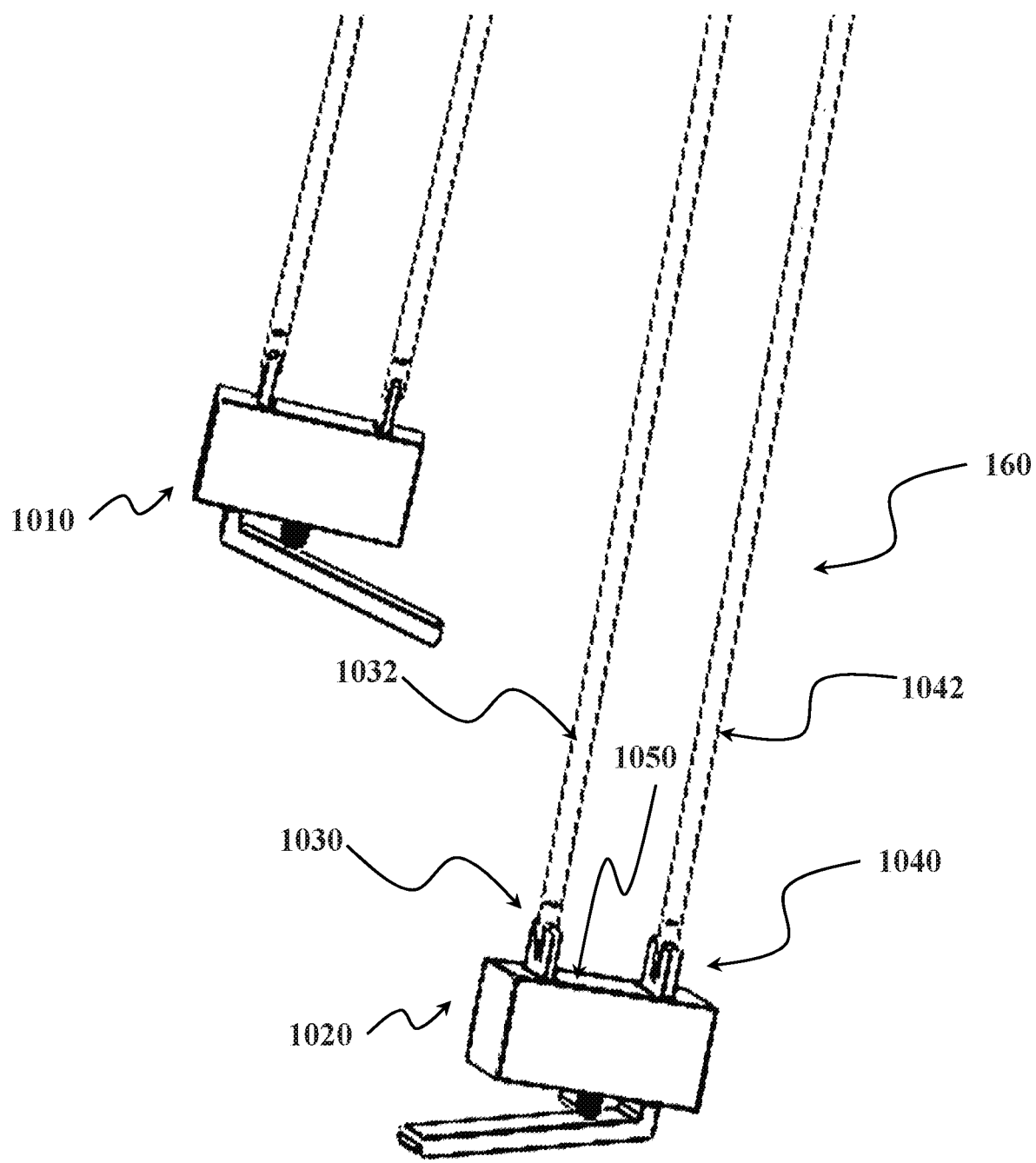
FIG. 10 is an isometric illustration of an implementation of switch components of a knee brace device.
Figure 11:
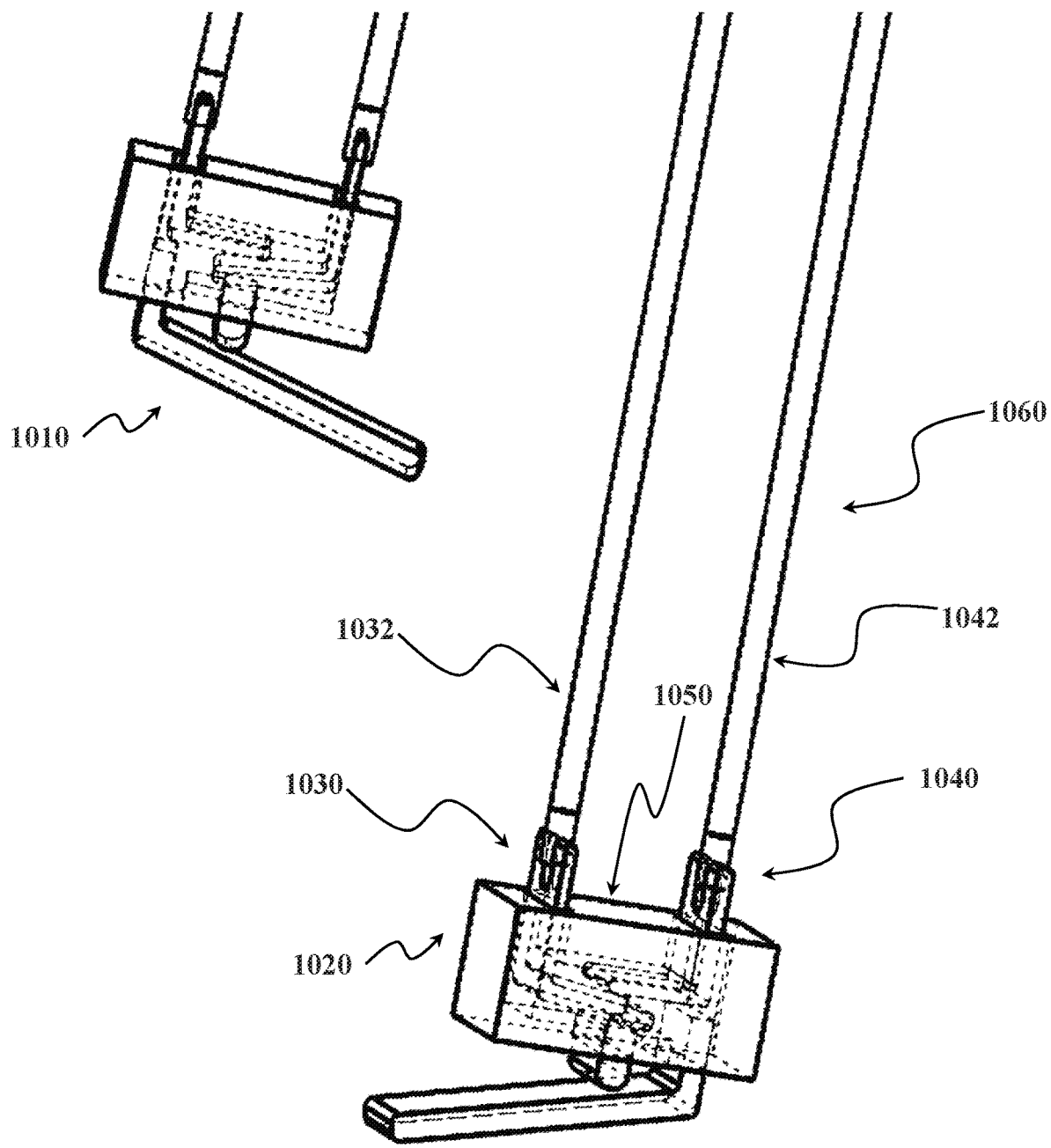
FIG. 11 is an isometric illustration of an implementation of switch components of a knee brace device.

Furthermore, in some implementations, base portion 790 is associated with, contains, or is attached to a control unit that operates in conjunction with the switch components (see FIGS. 10 and 11). It should be understood that in some implementations, the anchoring end 712 is inserted into and secured within base portion 790 via a through-hole aperture or channel. In other implementations, the anchoring end 712 can be secured through any include other attachment devices or connectors that permit translational movement and/or rotational motion (either clockwise or counter-clockwise) of the first segment 710.

In addition, the receiving end 714 can include provisions for movable connection to the second segment 720. For example, in FIG. 7, receiving end 714 includes a looped portion with a through-hole aperture that is sized and dimensioned to snugly receive a portion of second segment 720. In other implementations, the receiving end 714 may not include a looped portion, and instead can any include other attachment devices or connectors that permit translational movement and/or rotational motion (either clockwise or counter-clockwise) of the second segment 720.

Similarly, the second segment 720 can be understood to extend between a third end portion or connecting portion 722 and a fourth end portion or mounting portion 724. The connecting portion 722 is the portion of the second segment 720 that is sized and dimensioned to slide snugly into the aperture formed in the looped portion of the receiving end 714 identified above. Furthermore, mounting portion 724 at the opposite end of the second segment 720 is configured to be inserted and/or secured with the vibration component. Thus, a component housing 770 can be seen in FIG. 7 to which the mounting portion 724 is movably connected. Extending outward from the component housing 770 is a stimulator portion 772 of the third component 530, which will be discussed in further detail with reference to FIGS. 8 and 9 below.

In different implementations, the device can include provisions for allowing adjustment of the spatial position and/or orientation of the vibration components. In some implementations, the connection between each segment may be loosened to permit a user to reposition one or more portions of the arm or vibration component. For example, two portions may be connected by a screw mechanism, such that a user is able to unfasten and fasten the connections to allow for adjustments. In one implementation, some portions of the segments can include threading and/or threaded holes. In some implementations, there can be any other mechanism that is configured to allow the secure connection between two portions as well as linear and/or rotational motion.

In different implementations, the wide range of spatial adjustments noted above are made possible through the arm mechanism and connection of each portion, as described above, which allows each vibration component to achieve five degrees of freedom, including three degrees of freedom achieved by rotational motion and two degrees of freedom achieved by translational motion. In FIG. 7, a magnified isolated view of a vibration component and associated arm is depicted. It can be seen that first segment 710 is configured to move translationally back and forth (or up and down) in a first direction 702 substantially parallel to the lateral axis 180. In addition, the first segment 710 is capable of rotational motion about a fixed axis (here, its longitudinal axis 706, or the direction along which first segment 710 is elongated). Thus the first segment 710 can move or turn 360 degrees relative to the base portion 790, as represented by arrow 704.

In addition, second segment 720 is configured to move translationally back and forth (or up and down) in a second direction 752 substantially parallel to the vertical axis 190. In addition, the second segment 720 is capable of rotational motion about a fixed axis (here, its longitudinal axis 756, or the direction along which second segment 720 is elongated). In other words, the second segment 720 can move or turn 360 degrees relative to the first segment 710, as represented by arrow 754.

Furthermore, the component housing 770 is capable of rotational motion relative to the second segment 720, as represented by arrow 756. Thus, in some implementations, the position of each vibration components can be understood to be highly adjustable, and can be repositioned over a wide range with great sensitivity.

As noted earlier, the vibration components are configured to generate vibrations. In some implementations, the vibrations generated by the vibration components are of generally lower frequencies. In different implementations, the vibration components can be configured to produce vibrations mechanically, electromagnetically, or by shockwave or ultrasound. Furthermore, in some cases, the vibrations are generated mechanically and applied locally to the injured knee in a manner designed to help stimulate the formation of new blood vessels (angiogenesis) thereby increasing the blood supply to the afflicted knee and associated tendons, muscles and joints and thereby accelerating recovery. In addition, to reduce knee pain, the knee and the region around the knee can be contacted with the vibrating component as applied by the device. Thus, rather than the use of cumbersome, require time, and often expensive whole body vibration apparatuses, the device presented here allows for portability and easy, comfortable usability in different environments and during different everyday activities. The vibrational benefits can be provided as part of a person's normal routine, with little interference in their day-to-day schedule.

Figure 8:
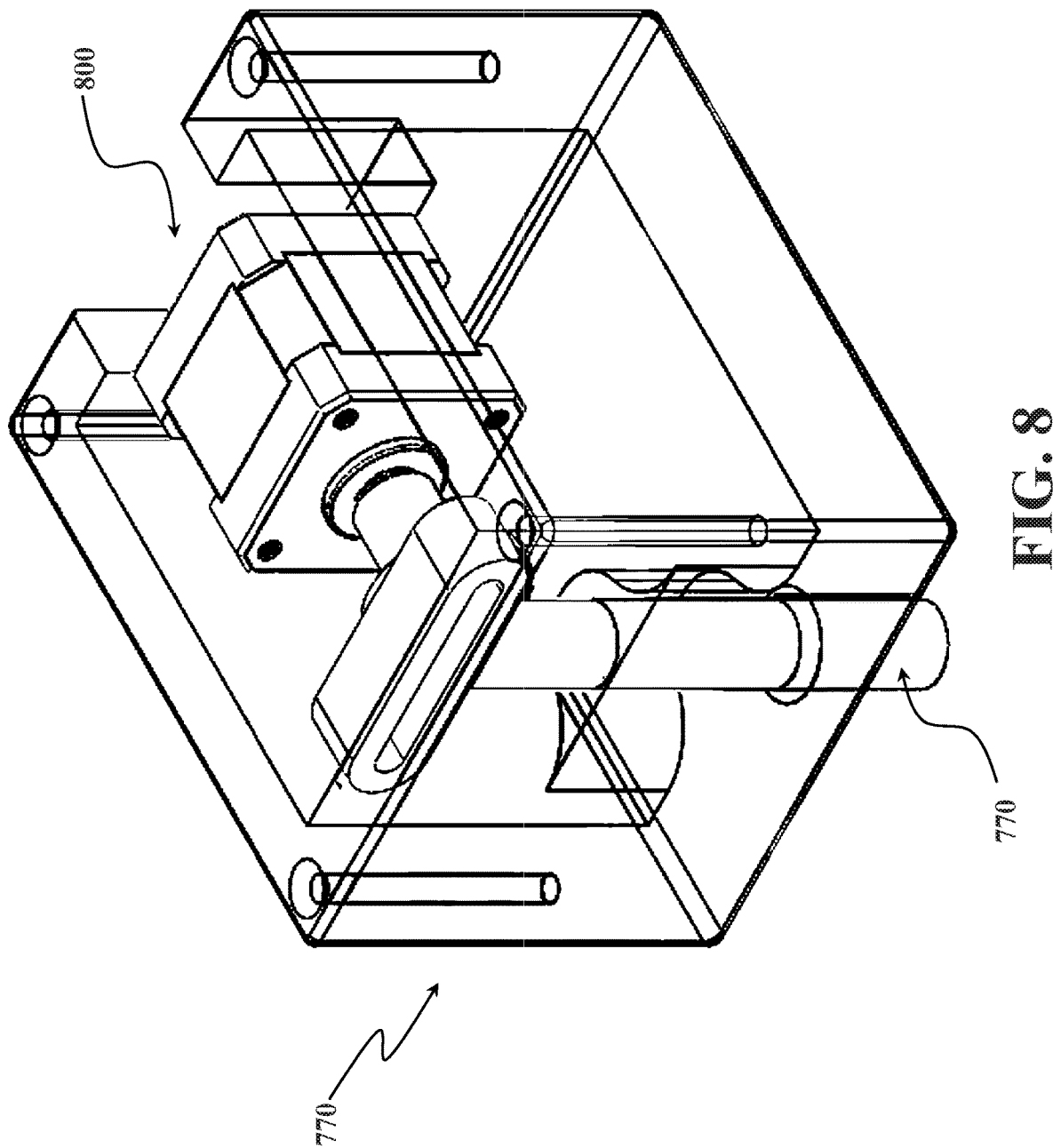
FIG. 8 is an illustration of an implementation of a vibration component of a knee brace device.
Figure 9:
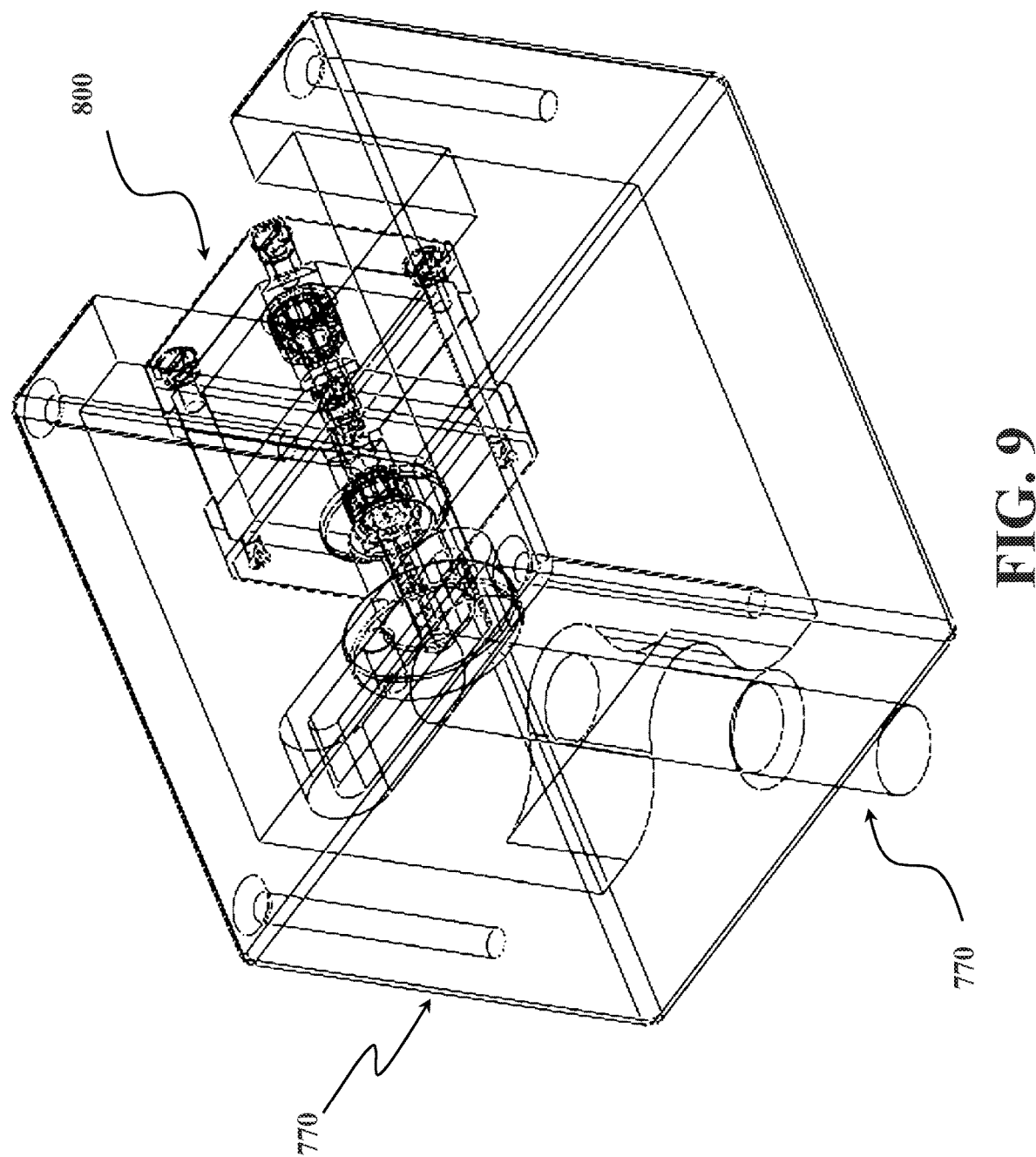
FIG. 9 is an illustration of an implementation of a vibration component of a knee brace device.

For purposes of clarity, FIGS. 8 and 9 depict an isolated view of one implementation of a vibration component. As noted above, the vibration components are configured to produce mild to moderate vibrations. In some cases, the vibration intensity may be comparable to those produced by a vibrating mobile telephone or a massage device. However, in different implementations, the level of vibration intensity can be adjusted and fine-tuned for an individual's needs and comfort. Thus, the frequency of vibration may range from approximately 5 to 500 oscillations per second (i.e., around 5 to 500 Hz). In one implementation, the frequency of vibration applied to the knee region is generally accepted to range between 10 Hz and 50 Hz. In some implementations, the intensity may be adjusted by a control panel available directly on the device. However, in other implementations, the device may include an option for a remote control or a web or mobile application through which the vibration settings may be adjusted.

In different implementations, the mechanism for the vibration itself can be achieved using known various technologies and located in the component housing 770. As one example, a motor can drive a gear on which is set a weight mounted off-center on the gear. When the motor spins the gear/weight off-center combination can cause a vibration. In another example, presented in FIGS. 8 and 9, the mechanism is dependent on a stepper motor 800 (either five-phase or two-phase), which generally includes a stator and rotor. The rotor can be made up of three components: a first rotor, a second rotor, and a permanent magnet. The circular motion of the motor can then be translated into linear movement at the stimulator shaft portion ("stimulator portion") 772, which extends through the component housing 770 and protrudes outside of the housing to provide a vibrational contact surface with the leg or with the clothing covering the leg. In other words, the stimulator portion 772 can include an elongated rod or bar which projects from the outer surface of the housing, providing a vibrating surface which can be arranged to contact the targeted region of the knee. In some cases, a vibration nozzle might be used. However, it should be understood that in other implementations, any other type of motor can be used to generate the requisite vibration.

In addition, the size of the vibration components can vary in different implementations. For example, the component housing can be approximately between 2 and 10 cm in length, height, and/or width. The stimulator portion 772 may protrude from the housing by approximately 0.5 to 50 mm, and have a diameter of approximately 0.5 to 2 cm. However, in other implementations, the dimensions of the housing and the stimulator portion can vary widely, beyond the ranges identified, in order to best accommodate the needs of each individual.

In different implementations, the vibration components may be battery powered. The batteries can be rechargeable and/or replaceable. In one implementation, the device may include an adaptor that can allow all of the vibration components to be recharged by a single connection to an electrical power source. In some other implementations, the device can be powered by an electrical source or run on both battery and electrical power.

The device can also include provisions for activation of the different vibration components. Referring now to FIGS. 10 and 11, additional details are provided with respect to the activation or switch portion of the knee device. In FIGS. 10 and 11, an isolated magnified view of the switch portion 160 of a knee device is depicted. FIG. 10 presents an isometric view of an implementation of the switch portion, and FIG. 11 presents a similar view with dotted lines to indicate components of the switch portion that are not visible in FIG. 11.

As shown in FIGS. 10 and 11, in some implementations, the knee device can include a first switch device ("first switch") 1010 and a second switch device ("second switch") 1020. In one implementation, each switch includes a plurality of terminals. In FIGS. 10 and 11, second switch 1020 is shown to include a first terminal 1030 and a second terminal 1040 disposed along an upper surface 1050 of the switch. It should be understood in one implementation, each switch can include at least two individual terminals. Furthermore, in some implementations, each terminal is connected to a wire that allows electrical current to travel between the switch and a corresponding control unit. Thus, the first terminal 1030 is connected to first wires 1032 and the second terminal 1040 is connected to second wires 1042. The wires can be highly resilient and flexible, as well as substantially thin or narrow. A switch can be connected via wires to an electric control system or transmitter, as referred to in FIG. 7 (see control unit in base portion 790).

In different implementations, each switch can be configured to provide feedback to and activation of different vibration components. In the device presented here, the first switch 1010 is connected to a control unit that is further connected to the first component and the second component. Thus, activation of the first switch 1010 results in an "on" state for both the first component and the second component. Similarly, the second switch 1020 is connected to a control unit that is further connected to the third component. Activation of the second switch 1020 results in an "on" state for the third component. Furthermore, in some implementations, a connection or wire for transmitting commands to the vibration component extends between the control unit and the vibration component via a hollow interior of the arm assembly, or along the outer surface of the arm assembly.

In some implementations, each switch can include an activation mechanism. For example, in FIGS. 10 and 11, the first switch 1010 includes a stepper mechanism 1060. Thus, the switch can be positioned along a person's foot (i.e., beneath the sole of the foot or shoe) and contact with the floor can compress the stepper mechanism and activate the switch. In cases where the switch is placed on the bottom of the shoe, various adhesives or connective mechanisms may be used. In some implementations, the switch includes an "on-off" button or lever which has a sensitivity allowing it to be compressed, and thereby is activated by the pressure typically applied under a person's foot during ambulation. In one implementation, the switch is a micro-switch.

As an example, in some implementations, the first switch can be positioned in a heel region via adhesive, and the second switch can be positioned toward a forefoot region by a hook and loop material. The adhesive can be reusable or replaceable. In this example, the first component and the second component will be active or "on" during the periods in which a person's heel is on the floor and pressure is exerted on the first switch. Similarly, the third component will be active or "on" during the periods in which the person's forefoot is on the floor and pressure is exerted on the second switch.

In everyday use, because a person's feet are initially flat on the floor, both microswitches would be activated from the weight of the person. Each wire would then carry a signal to the corresponding control unit which indicates that each microswitch is activated and turns on the three vibration components. During the walking process, when a portion of a foot near a microswitch is not on the ground, there will be insufficient pressure on that microswitch to activate it. As any foot portion is placed on the ground, the pressure then on the corresponding microswitch will activate it. Each microswitch, upon activation, induces the wire to carry a signal to the corresponding control unit indicating that that the specified microswitch is currently activated; this signal continues as long as that microswitch remains activated by the pressure. Thus, in some implementations, the duration of the activation and corresponding vibration is related to the stance phase—the time period during which a particular portion of the foot is supporting the body above it. The duration of the non-activation corresponds to the swing phase—the time period during which the particular portion of the foot is swinging or free from (not in contact with) the walking surface.

Figure 12:
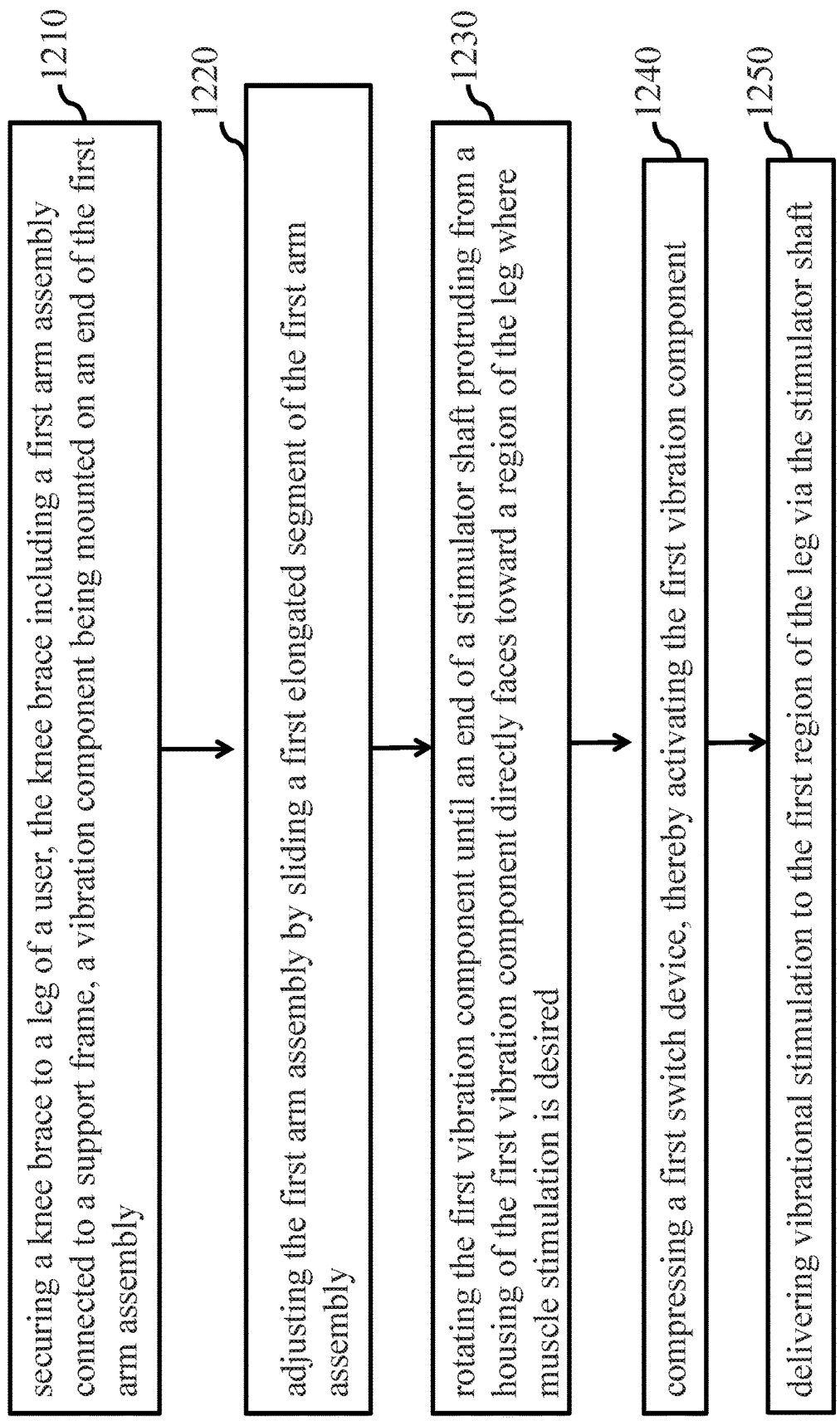
FIG. 12 is a flow chart depicting an implementation of a method of providing stimulation to muscles using the disclosed knee brace device.

Referring now to FIG. 12, a flow chart depicting an implementation of a method of stimulating muscles, or providing stimulation to muscles, is shown. Generally, the method can include a first step 1210 of securing a knee brace to a leg of a user, where the knee brace includes a first arm assembly connected to a support frame, and a vibration component is mounted on an end of the first arm assembly, as well as a second step 1220 of adjusting the first arm assembly by sliding a first elongated segment of the first arm assembly along a first direction that is substantially perpendicular to a first longitudinal axis of the leg, where the first elongated segment is elongated in the first direction. As described above, the knee brace can include a plurality of arm assemblies; thus, while only one arm assembly is identified in the first step 1210, it should be understood that additional arm assemblies can be adjusted. In addition, the method includes a third step 1230 of rotating the first vibration component until an end of a stimulator shaft protruding from a housing of the first vibration component directly faces toward a region of the leg where muscle stimulation is desired, a fourth step 1240 of compressing a first switch device, thereby activating the first vibration component, and a fifth step 1250 of delivering vibrational stimulation to the first region of the leg via the stimulator shaft.

In some implementations, the method can include additional steps or features. For example, the step of adjusting the first arm assembly can further include sliding a second elongated segment of the first arm assembly along a second direction that is substantially perpendicular to the first direction, where the second elongated segment is elongated in the second direction. In addition, the step of adjusting the first arm assembly can also include rotating the first elongated segment about a second longitudinal axis of the first elongated segment. In another implementation, adjusting the first arm assembly further includes rotating the second elongated segment about a third longitudinal axis of the second elongated segment, the third longitudinal axis being substantially perpendicular to the first longitudinal axis. Furthermore, in some implementations, compressing the first switch device further includes the user taking at least a first step with the leg on which the knee device is secured. In one implementation, the method can also include ceasing delivery of the vibrational stimulus when the compressive force on the first switch device is released.

While various implementations have been described, the description is intended to be exemplary, rather than limiting, and it is understood that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various examples for the purpose of streamlining the disclosure. This method of disclosure is not to be interpreted as reflecting an intention that the claims require more features than are expressly recited in each claim. Rather, as the following claims reflect, inventive subject matter lies in less than all features of a single disclosed example. Thus the following claims are hereby incorporated into the Detailed Description, with each claim standing on its own as a separately claimed subject matter.

What is claimed is:

1. A device for applying local vibration to knee muscles of a person while walking, the device comprising:
    a support frame, the support frame including an intermediate portion extending between an upper bar and a lower bar, the intermediate portion including a primary hinge, the primary hinge being configured to facilitate bending of the upper bar relative to the lower bar;
    a first arm assembly, the first arm assembly including a first elongated segment and a second elongated segment, a first end portion of the first elongated segment being adjustably secured to the upper bar, a second end portion of the first elongated segment being adjustably secured to a third end portion of the second elongated segment;

a first vibration component mounted on a fourth end portion of the second elongated segment, the first vibration component being configured to generate vibrations, and a first shell, the first shell being attached to the upper bar, the first shell including a first cuff portion sized and dimensioned to wrap around a thigh region of the person.

2. The device of claim 1, further comprising a second arm assembly and a second vibration component, wherein the second arm assembly is adjustably secured to the lower bar, and the second vibration component is mounted on the second arm assembly.

3. The device of claim 2, further comprising a third arm assembly and a third vibration component, wherein the third arm assembly is adjustably secured to the upper bar, and the third vibration component is mounted on the third arm assembly.

4. The device of claim 1, further comprising a first switch device, wherein the first switch device is activated in response to a compressive force.

5. The device of claim 4, wherein the first vibration component is configured to generate vibrations in response to an activation signal generated by the first switch device.

6. The device of claim 3, further comprising a first switch device and a second switch device, wherein the first vibration component is configured to generate vibrations in response to an activation signal generated by the first switch device, and wherein the second vibration component is configured to generate vibrations in response to an activation signal generated by the second switch device.

7. The device of claim 6, wherein the third vibration component is configured to generate vibrations in response to the activation signal generated from the first switch device.

8. The device of claim 1, wherein the first elongated segment is capable of both translational motion and rotational motion.

9. The device of claim 1, wherein the second elongated segment is capable of both translational motion and rotational motion.

10. The device of claim 1, wherein the first vibration component is capable of rotational motion.

11. The device of claim 1, wherein the first vibration component has five degrees of freedom.

12. The device of claim 1, further comprising a second shell, the second shell being attached to the lower bar, the second shell including a second cuff portion sized and dimensioned to wrap around a calf region of the person.

13. The device of claim 5, further comprising a control unit, the control unit being configured to receive the activation signal and activate a motor in the first vibration component.

14. A method of providing stimulation to muscles, the method comprising:

securing a knee brace to a leg of a user, the knee brace including a first arm assembly connected to a support frame, a vibration component being mounted on an end of the first arm assembly;

adjusting the first arm assembly by sliding a first elongated segment of the first arm assembly along a first direction that is substantially perpendicular to a first longitudinal axis of the leg, wherein the first elongated segment is elongated in the first direction;

rotating the vibration component until an end of a stimulator shaft protruding from a housing of the vibration component directly faces a region of the leg where muscle stimulation is desired;

compressing a first switch device, thereby activating the vibration component; and delivering vibrational stimulation to the region of the leg via the stimulator shaft.

15. The method of providing stimulation to muscles of claim 14, wherein adjusting the first arm assembly further comprises sliding a second elongated segment of the first arm assembly along a second direction that is substantially perpendicular to the first direction, wherein the second elongated segment is elongated in the second direction.

16. The method of providing stimulation to muscles of claim 14, wherein adjusting the first arm assembly further comprises rotating the first elongated segment about a second longitudinal axis of the first elongated segment.

17. The method of providing stimulation to muscles of claim 16, wherein adjusting the first arm assembly further comprises rotating the second elongated segment about a third longitudinal axis of the second elongated segment, the third longitudinal axis being substantially perpendicular to the first longitudinal axis.

18. The method of providing stimulation to muscles of claim 14, wherein compressing the first switch device further comprises the user taking at least a first step with the leg on which the knee device is secured.

19. The method of providing stimulation to muscles of claim 14, further comprising ceasing delivery of the vibrational stimulation when the compressive force on the first switch device is released.

\* \* \* \* \*